(12) United States Patent
Suzuki

(10) Patent No.: US 9,333,148 B2
(45) Date of Patent: May 10, 2016

(54) POLYMERIZABLE COMPOSITION AND DENTAL MATERIAL

(75) Inventor: Kenji Suzuki, Kurashiki (JP)

(73) Assignee: KURARAY NORITAKE DENTAL INC., Kurashiki-shi (JP)

( * ) Notice: Subject to any disclaimer, the term of this patent is extended or adjusted under 35 U.S.C. 154(b) by 648 days.

(21) Appl. No.: 13/501,118

(22) PCT Filed: Oct. 19, 2010

(86) PCT No.: PCT/JP2010/006201
§ 371 (c)(1),
(2), (4) Date: Apr. 10, 2012

(87) PCT Pub. No.: WO2011/048802
PCT Pub. Date: Apr. 28, 2011

(65) Prior Publication Data
US 2012/0196952 A1    Aug. 2, 2012

(30) Foreign Application Priority Data
Oct. 23, 2009   (JP) ................................. 2009-244795

(51) Int. Cl.
*A61K 6/083* (2006.01)
*A61K 6/00* (2006.01)
*C08F 265/06* (2006.01)
*C08F 287/00* (2006.01)
*C08G 81/02* (2006.01)

(52) U.S. Cl.
CPC ............... *A61K 6/083* (2013.01); *A61K 6/0023* (2013.01); *A61K 6/0052* (2013.01); *C08F 265/06* (2013.01); *C08F 287/00* (2013.01); *C08G 81/021* (2013.01)

(58) Field of Classification Search
CPC ............................ A61K 6/0023; A61K 6/083
USPC ......................................................... 523/117
See application file for complete search history.

(56) References Cited

U.S. PATENT DOCUMENTS

| 5,318,999 | A | 6/1994 | Mitra et al. |
| 5,449,703 | A * | 9/1995 | Mitra et al. ..................... 522/57 |
| 2001/0003759 | A1 | 6/2001 | Sato et al. |
| 2002/0061938 | A1 | 5/2002 | Hino |
| 2009/0108241 | A1 * | 4/2009 | Ogura et al. .................. 252/586 |

FOREIGN PATENT DOCUMENTS

| CA | 2 715 384 A1 | 8/2009 |
| JP | 9 67223 | 3/1997 |
| JP | 10 139613 | 5/1998 |
| JP | 10 182329 | 7/1998 |
| JP | 2000 159621 | 6/2000 |
| JP | 2001 89693 | 4/2001 |
| JP | 2002 40657 | 2/2002 |
| JP | 2002 226316 | 8/2002 |
| JP | 2006 282714 | 10/2006 |
| JP | 2006282714 A * | 10/2006 |
| JP | 2007 126527 | 5/2007 |
| WO | WO 93/20164 A1 | 10/1993 |
| WO | 2007 029783 | 3/2007 |

OTHER PUBLICATIONS

English machine translation of Kitano et al. (JP 2006282714); Aug. 14, 2014.*
International Search Report Issued Nov. 30, 2010 in PCT/JP10/06201 Filed Oct. 19, 2010.
Office Action issued in EP Application No. 10 824 654.7, dated Jul. 7, 2015.

* cited by examiner

*Primary Examiner* — Michael Pepitone
(74) *Attorney, Agent, or Firm* — Oblon, McClelland, Maier & Neustadt, L.L.P.

(57) ABSTRACT

The present invention provides a polymerizable composition that is suitably used as a temporary cement for implant use and a mobile tooth-fixing material. The present invention is a polymerizable composition that includes an acrylic block copolymer (a) having at least one polymer block A that mainly contains a (meth)acrylic acid ester unit and that functions as a hard segment and at least one polymer block B that mainly contains an acrylic acid ester unit and that functions as a soft segment, a polymerizable monomer (b), and a polymerization initiator (c).

18 Claims, No Drawings

POLYMERIZABLE COMPOSITION AND DENTAL MATERIAL

REFERENCE TO PRIOR APPLICATIONS

This application is a 371 of PCT/JP2010/006201, filed Oct. 19, 2010. Priority to Japanese patent application No. 2009-244795, filed Oct. 23, 2009, is claimed.

TECHNICAL FIELD

The present invention relates to a polymerizable composition that is suitable for application to biological tissues, particularly suitable as a temporary cement for implant use and a mobile tooth-fixing material, and relates to a dental material using the polymerizable composition.

BACKGROUND ART

Adhesive materials or filling materials are used for restorative treatment of teeth, bones, etc. Polymerizable compositions containing a polymerizable monomer, a polymerization initiator, a filler, etc., are generally used as such adhesive materials or filling materials. Polymerizable compositions for restorative treatment of teeth, bones, etc., can be roughly classified into two types depending on the hardness after curing. One type is a soft material, a cured product of which is flexible, to be used as an adhesive material, a shock absorber, etc., with respect to biological tissues, such as a temporary sealing material, a rebase for denture base, and an artificial cartilage. With the recent development of dental care, there is a glowing demand for new soft materials.

For example, dental treatment by implantation is widely used in recent years for the patients who have lost their teeth due to aging, etc. An implant is composed of an artificial tooth root to be embedded directly in the jaw bone, a tooth crown to be placed thereabove, and a tooth base, called an abutment, which engages the artificial tooth root and the tooth crown. These parts are bonded together at the time of use. For the bonding, a temporary cement is used, but the bonded portion is required to be removable because the implant occasionally needs to be detached for maintenance such as washing. Therefore, a cured product of the temporary cement is required to have excellent flexibility. The temporary cement also is required to have appropriate viscosity and forming property before curing so as to have excellent handling property. Further, it is required to have good adhesive properties with respect to metals and ceramics.

Meanwhile, the growth of periodontal disease causes gingival recession also due to aging, etc., making it difficult to support teeth sufficiently. As a result, the teeth become loose and lost easily. These loose teeth are called mobile teeth. To treat such a mobile tooth, a method of fixing the mobile tooth to a sound tooth using a mobile tooth-fixing material is employed. The mobile tooth-fixing material needs to be removed after recovery, and thus is required to be removable. It also is required not to break due to bending distortion to be applied continuously during the fixing until recovery. For this reason, a cured product of the mobile tooth-fixing material is required to have excellent flexibility. The mobile tooth-fixing material also is required to have appropriate viscosity and forming property before curing so as to have excellent handling property. Further, it also is required to have good adhesive properties with respect to tooth structure. Furthermore, a cured product thereof is required to have excellent transparency and color stability from the viewpoint of the aesthetic value.

As a method for imparting flexibility to a polymerizable composition, it is known to add an elastomer. For example, Patent Literature 1 reports an example in which the impact resistance of a metallic color-shielding adhesive material set for dental use is improved by adding butadiene-methyl methacrylate-styrene copolymer powder, thereby imparting flexibility thereto. Further, Patent Literatures 2 to 4 report examples in which a dental composition to be used for denture base, etc., is made flexible by adding a styrene-diene block copolymer thereto, so that the stress relaxation properties and the adhesive properties to the denture base are improved. Further, Patent Literature 5 reports an example in which the long-term coloration/discoloration and water absorption properties of a dental coating material composition are improved by adding a styrene-based thermoplastic elastomer or a methyl methacrylate-butyl acrylate copolymer thereto.

CITATION LIST

Patent Literature

Patent Literature 1: JP 2002-226316 A
Patent Literature 2: JP 9(1997)-67223 A
Patent Literature 3: JP 10(1998)-139613 A
Patent Literature 4: JP 10(1998)-182329 A
Patent Literature 5: JP 2001-89693 A

SUMMARY OF INVENTION

Technical Problem

The metallic color-shielding adhesive material set for dental use of Patent Literature 1 has poor dispersibility and miscibility of the respective components because it contains an elastomer in powder form, and thus fails to satisfy the above-mentioned various properties such as transparency required as a temporary cement for implant use and a mobile tooth-fixing material.

In the dental compositions according to Patent Literatures 2 to 4, the styrene-diene block copolymer and the (meth) acrylate monomer have different polarities from each other, which causes a problem in their miscibility. Low miscibility causes adverse effects on the above-mentioned various properties required as a temporary cement for implant use and a mobile tooth-fixing material.

In the dental coating material composition of Patent Literature 5, in the case of using the styrene-based thermoplastic elastomer, there is a similar problem of miscibility with the (meth)acrylate monomer. Meanwhile, no block copolymer is exemplified as the methyl methacrylate-butyl acrylate copolymer.

It is therefore an object of the present invention to provide a polymerizable composition that is suitable as a temporary cement for implant use and a mobile tooth-fixing material. It is another object of the present invention to provide a dental material using the polymerizable composition.

Solution to Problem

The present invention that has achieved the above-mentioned objects is a polymerizable composition includes: an acrylic block copolymer (a) having at least one polymer block A that mainly contains a (meth)acrylic acid ester unit and that functions as a hard segment, and at least one polymer block B that mainly contains an acrylic acid ester unit and that functions as a soft segment; a polymerizable monomer (b); and a polymerization initiator (c).

The acrylic block copolymer (a) preferably has a molecular weight distribution Mw/Mn of 1.0 to 1.5. The acrylic block copolymer (a) is preferably inactive against a polymerizable group of the polymerizable monomer (b).

The polymerizable monomer (b) is preferably a (meth) acrylate polymerizable monomer.

The polymerizable composition of the present invention preferably further contains a polymerization accelerator (d). The polymerizable composition of the present invention preferably further contains a filler (e).

The polymerizable composition of the present invention is suitably used for application to biological tissues.

The present invention also is a dental cement using the above-mentioned polymerizable composition. This dental cement is optimally used as a temporary cement for implant use.

The present invention also is a mobile tooth-fixing material using the above-mentioned polymerizable composition.

The present invention also is a dental composite resin using the above-mentioned polymerizable composition.

Advantageous Effects of Invention

The polymerizable composition of the present invention has both good viscosity and forming property at the same time before curing and thus has excellent handling property. Further, it exhibits good adhesive properties to tooth structure, bones, and metals. Furthermore, a cured product of the polymerizable composition has excellent flexibility, transparency, and color stability. Accordingly, the polymerizable composition of the present invention can be applied suitably to biological tissues (such as teeth and bones, particularly teeth). As specific applications, the polymerizable composition of the present invention is optimally used as a temporary cement for implant use and a mobile tooth-fixing material, and also is suitably used as a dental cement and a dental composite resin.

DESCRIPTION OF EMBODIMENTS

The polymerizable composition of the present invention includes an acrylic block copolymer (a) having at least one polymer block A that mainly contains a (meth)acrylic acid ester unit and that functions as a hard segment, and at least one polymer block B that mainly contains an acrylic acid ester unit and that functions as a soft segment; a polymerizable monomer (b); and a polymerization initiator (c).

Acrylic Block Copolymer (a)

The acrylic block copolymer (a) to be used in the present invention has at least one polymer block A that mainly contains a (meth)acrylic acid ester unit and that functions as a hard segment (hereinafter referred simply as "polymer block A"), and at least one polymer block B that mainly contains an acrylic acid ester unit and that functions as a soft segment (hereinafter referred simply as "polymer block B"). Accordingly, the acrylic block copolymer (a) functions as an elastomer.

In the present invention, the term "mainly contain" means that the content of the corresponding monomer unit is at least 50 wt %, preferably at least 80 wt %, more preferably at least 90 wt %, in all monomer units (repeating units) in a polymer block.

The (meth)acrylic acid ester unit that constitutes the polymer block A is not particularly limited, as long as the polymer block A functions as a hard segment of an elastomer. As a (meth)acrylic acid ester, methacrylic acid ester is preferable, and examples thereof include methyl methacrylate, ethyl methacrylate, n-propyl methacrylate, isopropyl methacrylate, n-butyl methacrylate, s-butyl methacrylate, t-butyl methacrylate, isobutyl methacrylate, n-hexyl methacrylate, cyclohexyl methacrylate, isobornyl methacrylate, benzyl methacrylate, and phenyl methacrylate. Among these, methyl methacrylate, isobornyl methacrylate, and t-butyl methacrylate are preferable because the use of them allows the polymer block A to have high glass transition temperature and to exhibit high aggregation, so that a cured product of the polymerizable composition of the present invention exhibits excellent strength. The polymer block A may contain two or more types of (meth)acrylic acid ester units.

The content of the polymer block A in the acrylic block copolymer (a) preferably is within the range of 1 to 75 wt %, more preferably within the range of 1.5 to 60 wt %, further preferably within the range of 3 to 50 wt %. When the content of the polymer block A is within the range of 1 to 75 wt %, appropriate flexibility is imparted to a cured product of the polymerizable composition.

The acrylic acid ester unit that constitutes polymer block B is not particularly limited, as long as the polymer block B functions as a soft segment of an elastomer. Accordingly, even in the case where the polymer block A mainly contains an acrylic acid ester unit, this acrylic acid ester unit is different from an acrylic acid ester unit that is contained in the polymer block B as the main component. Examples of the acrylic acid ester include methyl acrylate, ethyl acrylate, n-propyl acrylate, isopropyl acrylate, n-butyl acrylate, isobutyl acrylate, s-butyl acrylate, t-butyl acrylate, n-hexyl acrylate, cyclohexyl acrylate, 2-ethylhexyl acrylate, dodecyl acrylate, lauryl acrylate, stearyl acrylate, 2-methoxyethyl acrylate, and 2-(N,N-dimethylaminoethyl) acrylate. Among these, n-butyl acrylate, 2-ethylhexyl acrylate are preferable because the use of them allows the polymer block B to have low glass transition temperature, so that a cured product of the polymerizable composition of the present invention exhibits excellent flexibility. The polymer block B may contain two or more types of acrylic acid ester units.

The content of the polymer block B in the acrylic block copolymer (a) is preferably within the range of 25 to 99 wt %, more preferably within the range of 40 to 98.5 wt %, further preferably within the range of 50 to 97 wt %. When the content of the polymer block A is within the range of 25 to 99 wt %, appropriate flexibility is imparted to a cured product of the polymerizable composition.

Concerning the polymer block A and the polymer block B, the acrylic acid ester unit that constitutes the polymer block B may be contained in the polymer block A, and the (meth) acrylic acid ester unit that constitutes the polymer block A may likewise be contained in the polymer block B, as long as the effects of the present invention are not impaired. Further, other monomer units may be contained in these polymer blocks, as long as the effects of the present invention are not impaired. Examples of such other monomer include a (meth) acrylic acid ester having a functional group such as 2-hydroxyethyl (meth)acrylate, 2-aminoethyl (meth)acrylate, glycidyl (meth)acrylate, and tetrahydrofurfuryl (meth)acrylate; a vinyl monomer having a carboxyl group such as (meth) acrylic acid, maleic acid, and maleic acid anhydride; (meth) acrylamide; an aromatic vinyl monomer such as styrene, alpha-methylstyrene, and p-methylstyrene; a conjugate diene monomer such as butadiene and isoprene; an olefin monomer such as ethylene and propylene; and a lactone monomer such as epsilon-caprolactone and valerolactone.

The form of the bonding between the polymer block A and the polymer block B in the acrylic block copolymer (a) is not limited, as long as the polymer block A and the polymer block B are bonded to each other, and may be any one of the bonding forms selected from a straight chain, a branched chain, and a radial pattern, or a combination of two or more of them. Among these, the polymer block A and the polymer block B are preferably bonded in the form of a straight chain, and examples thereof include, when the polymer block A is referred to as "A" and the polymer block B is referred to as "B", a diblock copolymer represented by A-B, a triblock copolymer represented by A-B-A, a tetrablock copolymer represented by A-B-A-B, and a pentablock copolymer represented by A-B-A-B-A. Above all, a diblock copolymer (A-B) and a triblock copolymer (A-B-A) are preferably used, and a triblock copolymer (A-B-A) is further preferably used, because of ease of producing the acrylic block copolymer (a) and excellent flexibility of a cured product of the polymerizable composition.

The weight-average molecular weight (Mw) of the acrylic block copolymer (a) to be used in the present invention is preferably within the range of 5000 to 500000, more preferably within the range of 10000 to 200000, further preferably within the range of 30000 to 150000, in view of the solubility of the acrylic block copolymer (a) in the polymerizable monomer (b) and the flexibility of a cured product of the polymerizable composition. It should be noted that the weight-average molecular weight (Mw) herein means a weight-average molecular weight in terms of polystyrene as determined by gel permeation chromatography (GPC).

The molecular weight distribution (weight-average molecular weight/number-average molecular weight: Mw/Mn) of the acrylic block copolymer (a) to be used in the present invention is preferably 1.0 to 1.5, more preferably 1.0 to 1.4, further preferably 1.0 to 1.3, because appropriate viscosity and forming property of the composition, and high flexibility of a cured product thereof are easily obtained.

The production method of the acrylic block copolymer (a) to be used in the present invention is not specifically limited, as long as a copolymer that satisfies the conditions of the present invention on the chemical structure can be obtained, and a method according to known techniques can be employed. In order to obtain a block copolymer with a narrow molecular weight distribution, a method of subjecting monomers as a structural unit to living polymerization is employed. Living polymerization allows a block copolymer even with a molecular weight distribution of 1.0 to 1.3 to be obtained. Example of the techniques for living polymerization include a method of performing polymerization using an organic rare earth complex as a polymerization initiator, a method of performing anionic polymerization in the presence of a mineral acid salt such as salts of alkali metals or alkaline earth metals using an organic alkali metal compound as a polymerization initiator, a method of performing anionic polymerization in the presence of an organoaluminium compound using an organic alkali metal compound as a polymerization initiator, and a method known as Atom Transfer Radical Polymerization (ATRP).

Among the above-mentioned production methods, the method of performing anionic polymerization in the presence of an organoaluminium compound using an organic alkali metal compound as a polymerization initiator allows a block copolymer with a narrower molecular weight distribution to be produced, high polymerization rate to be obtained, and living polymerization to be performed under comparatively moderate temperature conditions. Thus, the acrylic block copolymer (a) to be used in the present invention is preferably produced by anionic polymerization in the presence of an organoaluminium compound using an organic alkali metal compound as a polymerization initiator.

For example, as described in WO 2007/029783, a method of sequentially polymerizing the (meth)acrylic acid ester and the acrylic acid ester that form the respective polymer blocks in the acrylic block copolymer (a), in the presence of an organolithium compound and an organoaluminium compound represented by the following general formula:

$$AlR^1R^2R^3$$

(where $R^1$ denotes an alkyl group that may have a substituent, an alkoxy group that may have a substituent, or an aryloxy group that may have a substituent, and $R^2$ and $R^3$ each independently denote an alkyl group that may have a substituent, an alkoxy group that may have a substituent, or an aryloxy group that may have a substituent, or $R^2$ and $R^3$ may be coupled together to form an arylenedioxy group that may have a substituent), additionally using N,N,N',N'',N''-pentamethyl diethylene triamine or other tertiary amines; and an ether such as 1,2-dimethoxyethane and a crown ether represented by 12-crown-4, on an as-needed basis, can be employed to perform the above-mentioned anionic polymerization in the presence of an organoaluminium compound using an organic alkali metal compound as a polymerization initiator.

Examples of the aforementioned organolithium compound that can be used for producing the acrylic block copolymer (a) include alkyl lithiums such as methyl lithium, n-butyl lithium, sec-butyl lithium, and t-butyl lithium; aralkyl lithiums such as 1,1-diphenylhexyl lithium and diphenylmethyl lithium; phenyl lithium, and trimethylsiloxylithium.

Further, examples of the organoaluminium compound represented by the general formula include trimethyl aluminum, triethyl aluminum, triisobutyl aluminum, dimethyl(2,6-di-t-butyl-4-methylphenoxy)aluminum, diethyl(2,6-di-t-butyl-4-methylphenoxy)aluminum, diisobutyl(2,6-di-t-butyl-4-methylphenoxy)aluminum, methylbis(2,6-di-t-butyl-4-methylphenoxy)aluminum, ethylbis(2,6-di-t-butyl-4-methylphenoxy)aluminum, and isobutylbis(2,6-di-t-butyl-4-methylphenoxy)aluminum. Among these, isobutylbis(2,6-di-t-butyl-4-methylphenoxy)aluminum is preferably used from the viewpoint of the capability of suppressing side reactions during polymerization and the ease of handling.

The acrylic block copolymer (a) to be used in the present invention is suitably produced by living polymerization. However, when it is used for the polymerizable composition, the chain end of the acrylic block copolymer (a) is preferably terminated in order to prevent side reactions. Accordingly, the acrylic block copolymer (a) is preferably inactive against the polymerizable group of the polymerizable monomer (b). Being inactive against the polymerizable group means not to cause any chemical reaction such as polymerization initiation reaction and coupling reaction with the polymerizable group.

Polymerizable Monomer (b)

As the polymerizable monomer (b) to be used for the polymerizable composition of the present invention, a radical polymerizable monomer is suitably used. Specific examples of the radical polymerizable monomer in the polymerizable monomer (b) include esters, for example, of alpha-cyanoacrylic acid, (meth)acrylic acid, alpha-halogenated acrylic acid, crotonic acid, cinnamic acid, sorbic acid, maleic acid, and itaconic acid, (meth)acrylamide, (meth)acrylamide derivatives, vinyl esters, vinyl ethers, mono-N-vinyl derivatives, and styrene derivatives. As the polymerizable monomer (b), a (meth)acrylate polymerizable monomer is preferable from the viewpoint of the miscibility with the acrylic block copolymer (a).

As an example of the polymerizable monomer (b) in the present invention, a monofunctional monomer having one polymerizable group and a polyfunctional monomer having a plurality of polymerizable groups are mentioned.

Examples of the monofunctional monomer include 2-hydroxyethyl (meth)acrylate, 2-hydroxypropyl (meth)acrylate, 3-hydroxypropyl (meth)acrylate, 4-hydroxybutyl (meth)acrylate, 6-hydroxyhexyl (meth)acrylate, 10-hydroxydecyl (meth)acrylate, propylene glycol mono(meth)acrylate, glycerol mono(meth)acrylate, erythritol mono(meth)acrylate, N-methylol (meth)acrylamide, N-hydroxyethyl (meth)acrylamide, N,N-(dihydroxyethyl) (meth)acrylamide, methyl (meth)acrylate, ethyl (meth)acrylate, propyl (meth)acrylate, isopropyl (meth)acrylate, n-butyl (meth)acrylate, sec-butyl (meth) acrylate, t-butyl (meth)acrylate, isobutyl (meth)acrylate, n-hexyl (meth)acrylate, cyclohexyl (meth)acrylate, lauryl (meth)acrylate, cetyl (meth)acrylate, stearyl (meth)acrylate, isobornyl (meth)acrylate, benzyl (meth)acrylate, phenyl (meth)acrylate, 2,3-dibromopropyl (meth)acrylate, 3-(meth)acryloyloxypropyltrimethoxysilane, 11-(meth)acryloyloxyundecyltrimethoxysilane, and (meth)acrylamide. One of them may be used alone, or two or more types of them may be used in combination. Among these, methyl methacrylate, ethyl (meth)acrylate, n-butyl (meth)acrylate, sec-butyl (meth)acrylate, t-butyl (meth)acrylate, isobutyl (meth)acrylate, n-hexyl (meth)acrylate, cyclohexyl (meth)acrylate, and isobornyl (meth)acrylate are preferable because the miscibility with the acrylic block copolymer (a) and the flexibility of a cured product of the polymerizable composition are excellent. Methyl methacrylate, t-butyl (meth)acrylate, and isobornyl methacrylate are further preferable because the toughness of a cured product of the polymerizable composition is excellent in addition.

Further, the polymerizable composition of the present invention may contain an acidic group-containing polymerizable monomer as the polymerizable monomer (b) since good bond strength to teeth, bones, and metals can be obtained. Examples of such an acidic group-containing polymerizable monomer include a radical polymerizable monomer that has at least one acidic group such as phosphoric acid group, pyrophosphoric acid group, thiophosphoric acid group, phosphonic acid group, sulfonic acid group, and carboxylic acid group, together with a polymerizable group.

Examples of the polymerizable monomer having a phosphoric acid group include 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyicosyl dihydrogen phosphate, bis[2-(meth)acryloyloxyethyl] hydrogen phosphate, bis[4-(meth)acryloyloxybutyl] hydrogen phosphate, bis[6-(meth)acryloyloxyhexyl] hydrogen phosphate, bis[8-(meth)acryloyloxyoctyl] hydrogen phosphate, bis[9-(meth)acryloyloxynonyl] hydrogen phosphate, bis[10-(meth)acryloyloxydecyl] hydrogen phosphate, 1,3-di(meth)acryloyloxypropyl dihydrogen phosphate, 2-(meth)acryloyloxyethylphenyl hydrogen phosphate, 2-(meth)acryloyloxyethyl-2-bromoethyl hydrogen phosphate, bis[2-(meth)acryloyloxy-(1-hydroxymethyl)ethyl]hydrogen phosphate, and their acid chlorides, alkali metal salts, and ammonium salts. These may be used individually, or two or more types of them may be used in combination.

Among the above-mentioned examples of the acidic group-containing polymerizable monomer, the acidic group-containing polymerizable monomer preferably has a phosphoric acid group or a phosphonic acid group, and more preferably has a phosphoric acid group, because of excellent miscibility with the acrylic block copolymer (a) and good bond strength of the polymerizable composition to teeth, bones, and metals. Above all, the acidic group-containing polymerizable monomer preferably contains in its molecule an alkyl group or an alkylene group having 6 to 20 carbon atoms in the main chain, and it more preferably contains in its molecule an alkylene group having 8 to 12 carbon atoms in the main chain, as 10-(meth)acryloyloxydecyl dihydrogen phosphate does, for example.

Examples of the polyfunctional monomer include aromatic compound-based bifunctional polymerizable monomers, aliphatic compound-based bifunctional polymerizable monomers, and at least trifunctional polymerizable monomers.

Examples of the aromatic compound-based bifunctional polymerizable monomers include 2,2-bis((meth)acryloyloxyphenyl) propane, 2,2-bis[4-(3-(meth)acryloyloxy)-2-hydroxypropoxyphenyl]propane (commonly known as "Bis-GMA"), 2,2-bis(4-(meth)acryloyloxyethoxyphenyl) propane, 2, 2-bis(4-(meth)acryloyloxypolyethoxyphenyl) propane, 2,2-bis(4-(meth)acryloyloxydiethoxyphenyl) propane, 2,2-bis(4-(meth)acryloyloxytetraethoxyphenyl) propane, 2,2-bis(4-(meth)acryloyloxypentaethoxyphenyl) propane, 2,2-bis(4-(meth)acryloyloxydipropoxyphenyl) propane, 2-(4-(meth)acryloyloxydiethoxyphenyl)-2-(4-(meth)acryloyloxyethoxyphenyl)-propane, 2-(4-(meth)acryloyloxydiethoxyphenyl)-2-(4-(meth)acryloyloxyditriethoxyphenyl) propane, 2-(4-(meth)acryloyloxydipropoxyphenyl)-2-(4-(meth)acryloyloxytriethoxyphenyl) propane, 2,2-bis(4-(meth)acryloyloxypropoxyphenyl)propane, 2,2-bis(4-(meth)acryloyloxyisopropoxyphenyl)propane, and 1,4-bis(2-(meth)acryloyloxyethyl)pyromeritate. These may be used individually, or two or more types of them may be used in combination. Among these, 2,2-bis(4-(meth)acryloyloxypolyethoxyphenyl)propane is preferable because the miscibility with the acrylic block copolymer (a) and the strength of a cured product of the polymerizable composition are excellent. Particularly, a compound in which the average number of moles of added ethoxy group is 2.6 (commonly known as "D2.6E") is preferable.

Examples of the aliphatic compound-based bifunctional polymerizable monomers include glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth)acrylate, polyethylene glycol di(meth)acrylate, 1,3-butanediol di(meth)acrylate, 1,4-butanediol di(meth)acrylate, 1,6-hexanediol di(meth)acrylate, 2-ethyl-1,6-hexanediol di(meth)acrylate, 1,9-nonanediol di(meth)acrylate, 1,10-decanediol di(meth)acrylate, 1,2-bis(3-methacryloyloxy-2-hydroxypropoxy)ethane, and 2,2,4-trimethylhexamethylene bis(2-carbamoyloxyethyl) dimethacrylate (commonly known as "UDMA"). Among these, glycerol di(meth)acrylate, triethylene glycol di(meth)acrylate, neopentyl glycol di(meth)acrylate, 1,4-butanediol di(meth)acrylate, 1,6-hexanediol di(meth)acrylate, 2-ethyl- 1,6-hexanediol di(meth)acrylate, 1,9-nonanediol di(meth) acrylate, 1,10-decaneol di(meth)acrylate, and 2,2,4-trimethylhexamethylene bis(2-carbamoyloxyethyl) dimethacrylate are preferable because the miscibility with the acrylic block copolymer (a) and the handleability of the polymerizable composition to be obtained are excellent. These may be used individually, or two or more types of them may be used in combination.

Examples of the at least trifunctional polymerizable monomers include trimethylolpropane tri(meth)acrylate, trimethylolethane tri(meth)acrylate, trimethylolmethane tri(meth) acrylate, pentaerythritol tri(meth)acrylate, pentaerythritol tetra(meth)acrylate, dipentaerythritol penta(meth)acrylate, N,N-(2,2,4-trimethylhexamethylene)bis[2-(aminocarboxy) propane-1,3-diol] tetramethacrylate, and 1,7-diacryloyloxy-2,2,6,6-tetraacryloyloxymethyl-4-oxyheptane. Among these, trimethylolpropane tri(meth)acrylate is preferable because the miscibility with the acrylic block copolymer (a) is excellent.

One of the above-mentioned examples of the polymerizable monomer (b) may be used alone. However, it is preferable that a bifunctional polymerizable monomer and a monofunctional monomer be used in combination from the viewpoint of the curability of the polymerizable composition and the toughness and flexibility of a cured product thereof. The ratio in the combined use of them is not specifically limited, but the content of the bifunctional polymerizable monomer is preferably 1 to 75 wt %, more preferably 2.5 to 50 wt %, further preferably 5 to 25 wt %, when the total amount of the polymerizable monomer (b) is taken as 100 wt %. When the content of the bifunctional polymerizable monomer is 75 wt % or less, the toughness of a cured product of the polymerizable composition is rendered high, where the cured product is less likely to break. In this description, the phrase "total amount of the polymerizable monomer (b)" means the total amount of polymerizable monomers contained in the whole composition. For example, when an embodiment of a two-part type composition is employed in the present invention, it means the total weight of polymerizable monomers contained in the respective parts.

Further, the content of the acidic group-containing polymerizable monomer is not specifically limited, but is preferably 1 to 50 wt %, more preferably 1.5 to 25 wt %, further preferably 2.5 to 15 wt %, when the total amount of the polymerizable monomer (b) is taken as 100 wt %. When the content of the acidic group-containing polymerizable monomer is 1 wt % or more, good bond strength is obtained. Meanwhile, when the content of the acidic group-containing polymerizable monomer is 50 wt % or less, the miscibility of the polymerizable composition is maintained at an appropriate level.

Regarding the amount of the acrylic block copolymer (a) and the polymerizable monomer (b) to be used, 5 to 500 parts by weight of the acrylic block copolymer (a) is preferably used, and 10 to 250 parts by weight of the acrylic block copolymer (a) is more preferably used, with respect to 100 parts by weight of the total amount of the polymerizable monomer (b).

Polymerization Initiator (c)

The polymerization initiator (c) to be used in the present invention can be selected from polymerization initiators commonly used in the industrial field. Among them, polymerization initiators used for dental applications are preferably used. Particularly, a photopolymerization initiator (c-1) and a chemical polymerization initiator (c-2) are used independently or two or more of them are used appropriately in combination.

Examples of the photopolymerization initiator (c-1) include (bis)acylphosphine oxides, thioxanthones or the quaternary ammonium salts of thioxanthones, ketals, alpha-diketones, coumarins, anthraquinones, benzoin alkyl ether compounds, and alpha-amino ketone compounds.

Preferably, among these photopolymerization initiators, at least one selected from the group consisting of (bis)acylphosphine oxides and salts thereof, and alpha-diketones is used. This makes it possible to obtain a composition that has excellent photocurability in visible and near-ultraviolet ranges and sufficiently high photocurability regardless of which light source among a halogen lamp, light-emitting diode (LED), and xenon lamp is used.

In the (bis)acylphosphine oxides to be used as the photopolymerization initiator, examples of acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, and benzoyl di-(2,6-dimethylphenyl) phosphonate. Examples of the bisacylphosphine oxides include bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphenylphosphine oxide, bis-(2,6-dimethoxybenzoyl)phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, (2,5,6-trimethylbenzoyl)-2,4,4-trimethylpentylphosphine oxide, 2,4,6-trimethylbenzoylphenylphosphine oxide sodium salt, 2,4,6-trimethylbenzoylphenylphosphine oxide potassium salt, and 2,4,6-trimethylbenzoylphenylphosphine oxide ammonium salt. In addition, the compounds disclosed in JP 2000-159621 A also can be mentioned.

Among these (bis)acylphosphine oxides, 2,4,6-trimethylbenzoyldiphenylphosphine oxide, 2,4,6-trimethylbenzoylmethoxyphenylphosphine oxide, bis(2,4,6-trimethylbenzoyl)phenylphosphine oxide, and 2,4,6-trimethylbenzoylphenylphosphine oxide sodium salt are particularly preferable.

Examples of the alpha-diketones to be used as the above-mentioned photopolymerization initiator include diacetyl, dibenzyl, camphorquinone, 2,3-pentadione, 2,3-octadione, 9,10-phenanthrenquinone, 4,4'-oxybenzyl, and acenaphthenequinone. Among these, camphorquinone is particularly preferable since it has the maximum absorption wavelength in the visible light region.

As the chemical polymerization initiator (c-2) in the polymerization initiator (c) to be used in the present invention, an organic peroxide is preferably used. The organic peroxide to be used as the chemical polymerization initiator is not particularly limited and a known one can be used. Typical examples of the organic peroxide include ketone peroxide, hydroperoxide, diacyl peroxide, dialkyl peroxide, peroxyketal, peroxyester, and peroxydicarbonate.

Examples of the ketone peroxide to be used as the chemical polymerization initiator include methyl ethyl ketone peroxide, methyl isobutyl ketone peroxide, methylcyclohexanone peroxide, and cyclohexanone peroxide.

Examples of the hydroperoxide to be used as the chemical polymerization initiator include 2,5-dimethylhexane-2,5-dihydroperoxide, diisopropylbenzene hydroperoxide, cumene hydroperoxide, t-butyl hydroperoxide, and 1,1,3,3-tetramethylbutyl hydroperoxide.

Examples of the diacyl peroxide to be used as the chemical polymerization initiator include acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide.

Examples of the dialkyl peroxide to be used as the chemical polymerization initiator include di-t-butyl peroxide, dicumyl peroxide, t-butylcumyl peroxide, 2, 5-dimethyl-2, 5-di(t-butylperoxy)hexane, 1, 3-bis(t-butylperoxyisopropyl)benzene, and 2,5-dimethyl-2,5-di(t-butylperoxy)-3-hexyne.

Examples of the peroxyketal to be used as the chemical polymerization initiator include 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane, and 4, 4-bis(t-butylperoxy)valeric acid-n-butyl ester.

Examples of the peroxyester to be used as the chemical polymerization initiator include alpha-cumyl peroxyneodecanoate, t-butyl peroxyneodecanoate, t-butyl peroxypivalate, 2,2,4-trimethylpentylperoxy-2-ethyl hexanoate, t-amyl peroxy-2-ethylhexanoate, t-butyl peroxy-2-ethylhexanoate, di-t-butyl peroxyisophthalate, di-t-butyl peroxyhexahydroterephthalate, t-butyl peroxy-3,3,5-trimethylhexanoate, t-butyl peroxyacetate, t-butyl peroxybenzoate, and t-butyl peroxymaleic acid.

Examples of the peroxydicarbonate to be used as the chemical polymerization initiator include di-3-methoxy peroxydicarbonate, di-2-ethylhexyl peroxydicarbonate, bis(4-t-butylcyclohexyl)peroxydicarbonate, diisopropyl peroxydicarbonate, di-n-propyl peroxydicarbonate, di-2-ethoxyethyl peroxydicarbonate, and diallyl peroxydicarbonate.

Among these organic peroxides, diacyl peroxide is preferably used from the viewpoint of the comprehensive balance of safety, storage stability, and radical generation ability, and among the examples thereof, benzoyl peroxide is particularly preferably used.

The content of the polymerization initiator (c) to be used in the present invention is not particularly limited, but is preferably 0.001 to 30 parts by weight with respect to 100 parts by weight of the total amount of the polymerizable monomer (b) from the viewpoint of the curability, etc., of the composition to be obtained. When the content of the polymerization initiator (c) is less than 0.001 part by weight, there are cases where polymerization does not proceed sufficiently and stickiness occurs. Therefore, the content thereof is more preferably at least 0.05 part by weight, further preferably at least 0.1 part by weight. On the other hand, when the content of the polymerization initiator (c) exceeds 30 parts by weight in the case where the polymerization initiator itself has low polymerization performance, precipitation from the composition may occur. Therefore, the content thereof is more preferably 20 parts by weight or less, further preferably 15 parts by weight or less, most preferably 10 parts by weight or less.

The polymerizable composition of the present invention is not specifically limited, as long as it contains the above-mentioned acrylic block copolymer (a), the polymerizable monomer (b), and the polymerization initiator (c). The polymerizable composition of the present invention can be easily produced by a method known to those skilled in the art.

Polymerization Accelerator (d)

The polymerizable composition of the present invention preferably contains a polymerization accelerator (d). Examples of the polymerization accelerator (d) include amines, sulfinic acid and salts thereof, sulfite, bisulfite, aldehydes, thiourea compounds, organophosphorus compounds, borate compounds, barbituric acid derivatives, triazine compounds, copper compounds, tin compounds, vanadium compounds, halogen compounds, and thiol compounds.

Amines to be used as the polymerization accelerator (d) can be classified into aliphatic amines and aromatic amines. Examples of the aliphatic amines include: primary aliphatic amines such as n-butylamine, n-hexylamine, and n-octylamine; secondary aliphatic amines such as diisopropylamine, dibutylamine, and N-methylethanolamine; and tertiary aliphatic amines such as N-methyldiethanolamine, N-ethyldiethanolamine, N-n-butyldiethanolamine, N-lauryldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, triethanolamine, trimethylamine, triethylamine, and tributylamine. Among these, tertiary aliphatic amines are preferable from the viewpoint of the curability and storage stability of the composition. Particularly, N-methyldiethanolamine and triethanolamine are more preferably used.

Examples of the aromatic amines include N, N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, N, N-dimethylaniline, N,N-dimethyl-p-toluidine, N, N-dimethyl-m-toluidine, N,N-diethyl-p-toluidine, N,N-dimethyl-3,5-dimethylaniline, N, N-dimethyl-3, 4-dimethylaniline, N, N-dimethyl-4-ethylaniline, N, N-dimethyl-4-isopropylaniline, N, N-dimethyl-4-t-butylaniline, N,N-dimethyl-3,5-di-t-butylaniline, 4-N,N-dimethylaminobenzoic acid ethyl ester, 4-N,N-dimethylaminobenzoic acid methyl ester, N,N-dimethylaminobenzoic acid n-butoxyethyl ester, 4-N,N-dimethylaminobenzoic acid 2-(methacryloyloxy)ethyl ester, 4-N,N-dimethylaminobenzophenone, and butyl 4-dimethylaminobenzoate. Among these, at least one selected from the group consisting of N,N-di(2-hydroxyethyl)-p-toluidine, 4-N,N-dimethylaminobenzoic acid ethyl ester, N,N-dimethylaminobenzoic acid n-butoxyethyl ester, and 4-N,N-dimethylaminobenzophenone is used preferably because excellent curability can be imparted to the composition.

Examples of the sulfinic acid and salt thereof to be used as the polymerization accelerator (d) include p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, and calcium 2,4,6-triisopropylbenzenesulfinate. Sodium benzenesulfinate, sodium p-toluenesulfinate, and sodium 2,4,6-triisopropylbenzenesulfinate are particularly preferable.

As the sulfite and bisulfite to be used as the polymerization accelerator (d), sodium sulfite, potassium sulfite, calcium sulfite, ammonium sulfite, sodium bisulfite, and potassium bisulfite, for example, can be mentioned. Among these, sodium sulfite is preferably used from the viewpoint of curability.

Examples of the aldehydes to be used as the polymerization accelerator (d) include terephthalaldehyde and benzaldehyde derivatives. Examples of the benzaldehyde derivatives include dimethylaminobenzaldehyde, p-methyloxybenzaldehyde, p-ethyloxybenzaldehyde, and p-n-octyloxybenzaldehyde. Among these, p-n-octyloxybenzaldehyde is preferably used from the viewpoint of curability.

Examples of the thiourea compounds to be used as the polymerization accelerator (d) include 1-(2-pyridyl)-2-thiourea, thiourea, methylthiourea, ethylthiourea, N, N'-dimethylthiourea, N, N'-diethylthiourea, N, N'-di-n-propylthiourea, N, N'-dicyclohexylthiourea, trimethylthiourea, triethylthiourea, tri-n-propylthiourea, tricyclohexylthiourea, tetramethylthiourea, tetraethylthiourea, tetra-n-propylthiourea, and tetracyclohexylthiourea.

Examples of the organophosphorus compounds to be used as the polymerization accelerator (d) include triphenylphosphine, 2-methyltriphenylphosphine, 4-methyltriphenylphosphine, 2-methoxytriphenylphosphine, 4-methoxytriphenylphosphine, tri-n-butylphosphine, triisobutylphosphine, and tri-t-butylphosphine. Among these, triphenylphosphine and 2-methyltriphenylphosphine are preferably used from the viewpoint of curability.

The content of the polymerization accelerator (d) to be used for the present invention is not specifically limited, but 0.001 to 30 parts by weight of the polymerization accelerator (d) is preferably contained with respect to 100 parts by weight of the total amount of the polymerizable monomer (b) from the viewpoint of the curability of the composition to be obtained. When the content of the polymerization accelerator (d) is less than 0.001 part by weight, there are cases where polymerization does not proceed sufficiently and stickiness occurs. Therefore, the content is more suitably at least 0.05 part by weight, further suitably at least 0.1 part by weight. On the other hand, when the content of the polymerization initiator (d) exceeds 30 parts by weight in the case where the polymerization initiator itself has low polymerization performance, precipitation from the composition may occur. Therefore, the content thereof is more preferably 20 parts by weight or less, further preferably 10 parts by weight or less.

In the present invention, the chemical polymerization initiator (c-2) and the polymerization accelerator (d) may be combined to form a redox polymerization initiator. In this case, the chemical polymerization initiator (c-2) and the polymerization accelerator (d) are stored in separate containers from the viewpoint of storage stability. Accordingly, the dental polymerizable composition is provided as a product that at least includes a first part containing the chemical polymerization initiator (c-2) and a second part containing the polymerization accelerator (d). Preferably, the dental polymerizable composition is provided as a kit to be used in the form of a two-part composition composed of the first part and the second part. Further preferably, it is provided as a kit to be used as a two-paste type in which both parts are in paste form. When the composition is used as a two-paste type, it is preferable that the respective pastes be separated from each other during storage, and then immediately before the use, the two pastes be mixed and kneaded to allow chemical polymerization to proceed, or to allow chemical polymerization and photopolymerization to proceed in the case where a photopolymerization initiator is further contained therein, so as to be cured.

Filler (e)

In the polymerizable composition of the present invention, a filler (e) may be further contained in order to adjust the paste properties of the polymerizable composition before curing, and also to enhance the mechanical strength of a cured product thereof. As such a filler, an organic filler, an inorganic filler, and an organic-inorganic composite filler can be mentioned, for example.

As a material of the organic filler, polymethylmethacrylate, polyethylmethacrylate, methyl methacrylate-ethyl methacrylate copolymer, crosslinked polymethylmethacrylate, crosslinked polyethylmethacrylate, polyester, polyamide, polycarbonate, polyphenylene ether, polyoxymethylene, polyvinyl chloride, polystyrene, polyethylene, polypropylene, chloroprene rubber, nitrile rubber, ethylene-vinyl acetate copolymer, styrene-butadiene copolymer, acrylonitrile-styrene copolymer, and acrylonitrile-styrene-butadiene copolymer can be mentioned, for example. These may be used independently or may be used as a mixture of two or more of them. The shape of the organic filler is not particularly limited, and the particle size of the filler to be used can be selected appropriately.

As a material of the inorganic filler, quartz, silica, alumina, silica-titania, silica-titania-barium oxide, silica-zirconia, silica-alumina, lanthanum glass, borosilicate glass, soda glass, barium glass, strontium glass, glass ceramics, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass can be mentioned, for example. Also, these can be used independently or two or more of them may be mixed for use. The shape of the inorganic filler is not particularly limited, and amorphous fillers, spherical fillers, etc., can be appropriately selected for use.

The inorganic filler may be used after being subjected to surface pretreatment with a known surface-treating agent such as a silane coupling agent, as needed, in order to adjust the miscibility with the polymerizable monomer (b). Examples of the surface-treating agent include vinyltrimethoxysilane, vinyltriethoxysilane, vinyltrichlorosilane, vinyltri(beta-methoxyethoxy)silane, 3-methacryloyloxypropyltrimethoxysilane, 11-methacryloyloxyundecyltrimethoxysilane, 3-glycidoxypropyltrimethoxysilane, 3-mercaptopropyltrimethoxysilane, and 3-aminopropyltriethoxysilane.

A known method can be used as a method for the surface treatment, without specific limitation. For example, there are a method in which the above-mentioned surface-treating agent is added by spraying while vigorously stirring the inorganic filler, a method in which, after the inorganic filler and the above-mentioned surface-treating agent are dispersed or dissolved in a suitable solvent, the solvent is removed, and a method in which the alkoxy group in the above-mentioned surface-treating agent is converted into a silanol group through hydrolysis with an acid catalyst in an aqueous solution so as to be attached to the surface of the inorganic filler in the aqueous solution, from which water is thereafter removed. In any method, heating normally in the range of 50 to 150° C. allows the reaction between the surface of the inorganic filler and the above-mentioned surface-treating agent to complete, thereby allowing the surface to be treated.

An organic-inorganic composite filler can be obtained by adding a monomer compound to the aforementioned inorganic filler beforehand, making it into a paste, thereafter polymerizing it, and crushing it. As the organic-inorganic composite filler, TMPT filler (obtained by mixing trimethylolpropane methacrylate and silica filler, polymerizing it, and then crushing it), for example, can be used. The shape of the organic-inorganic composite filler is not particularly limited, and the particle size of the filler can be appropriately selected for use.

The average particle size of the filler (e) is preferably 0.001 to 50 µm, more preferably 0.001 to 10 µm, from the viewpoint of the handleability of the polymerizable composition to be obtained and the mechanical strength of a cured product thereof. In this description, the average particle size of the filler can be determined by an arbitrary method known to those skilled in the art. For example, it can be determined easily using a laser diffraction particle size distribution analyzer mentioned later in Examples.

The content of the filler (e) is not specifically limited, but is preferably 500 parts by weight or less, more preferably 250 parts by weight or less, further preferably 100 parts by weight or less, with respect to 100 parts by weight of the total amount of the acrylic block copolymer (a) and the polymerizable monomer (b), from the viewpoint of the handleability of the polymerizable composition to be obtained and the mechanical strength of a cured product thereof. When the content of the filler (e) is 500 parts by weight or less, the flexibility of a cured product is maintained at a good level.

As long as the effects of the present invention are not impaired, the polymerizable composition of the present invention may additionally contain other polymers such as natural rubber, synthetic polyisoprene rubber, liquid polyisoprene rubber and hydrogenated products thereof, polybutadiene rubber, liquid polybutadiene rubber and hydrogenated products thereof, styrene-butadiene rubber, chloroprene rubber, ethylene-propylene rubber, acrylic rubber, isoprene-isobutylene rubber, acrylonitrile-butadiene rubber, and styrene elastomer (e.g., polystyrene-polyisoprene-polystyrene block copolymer, polystyrene-polybutadiene-polystyrene block copolymer, poly(alpha-methylstyrene)-polybutadiene-poly(alpha-methylstyrene) block copolymer, poly(p-methylstyrene)-polybutadiene-poly(p-methylstyrene) block copolymer, or hydrogenated products thereof), in order to improve the properties such as flexibility and fluidity.

The polymerizable composition of the present invention may contain a softener, as needed. Examples of the softener include petroleum-based softeners such as paraffin, naphthene, and aromatic process oils, and vegetable oil-based softeners such as paraffin, peanuts oil, and rosin. These softeners may be used individually, or two or more types of them may be mixed for use. The content of the softener is not particularly limited, as long as the object of the present invention is not impaired, but is generally 300 parts by weight or less, preferably 100 parts by weight or less, with respect to 100 parts by weight of the total amount of the acrylic block copolymer (a) and the polymerizable monomer (b).

Further, the polymerizable composition of the present invention may contain a known additive within a range that does not reduce the performance. Examples of the additive include a polymerization inhibitor, an antioxidant, a pigment, a dye, an ultraviolet absorber, an organic solvent, and a thickener.

Examples of the polymerization inhibitor include hydroquinone, hydroquinone monomethyl ether, dibutyl hydroquinone, dibutyl hydroquinone monomethyl ether, t-butylcatechol, 2-t-butyl-4,6-dimethylphenol, 2,6-di-t-butylphenol, and 3, 5-di-t-butyl-4-hydroxytoluene. The content of the polymerization inhibitor is preferably 0.001 to 1.0 part by weight with respect to 100 parts by weight of the total amount of the acrylic block copolymer (a) and the polymerizable monomer (b).

The polymerizable composition of the present invention has both good viscosity and forming property at the same time before curing and thus is excellent in handling property. Further, it exhibits good adhesive properties to tooth structure, bones, and metals. Furthermore, a cured product of the polymerizable composition of the present invention is excellent in flexibility, transparency, and color stability. Accordingly, the polymerizable composition of the present invention can be used in applications that exploit such advantages, particularly, can be applied suitably to biological tissues (such as teeth and bones, particularly teeth). As specific applications, the polymerizable composition of the present invention is optimally used as a temporary cement for implant use and a mobile tooth-fixing material, and also is suitably used as a dental cement and a dental composite resin.

A suitable configuration example of the dental cement is shown below. The dental cement preferably contains 5 to 500 parts by weight of the acrylic block copolymer (a), 0.05 to 15 parts by weight of the polymerization initiator (c), and 0.05 to 20 parts by weight of the polymerization accelerator (d), with respect to 100 parts by weight of the total amount of the polymerizable monomer (b), and 0 to 500 parts by weight of the filler (e), with respect to 100 parts by weight of the total amount of the acrylic block copolymer (a) and the polymerizable monomer (b). It is more preferable to contain 10 to 250 parts by weight of the acrylic block copolymer (a), 0.1 to 10 parts by weight of the polymerization initiator (c), and 0.1 to 10 parts by weight of the polymerization accelerator (d), with respect to 100 parts by weight of the total amount of the polymerizable monomer (b), and 10 to 250 parts by weight of the filler (e), with respect to 100 parts by weight of the total amount of the acrylic block copolymer (a) and the polymerizable monomer (b).

A suitable configuration example of the temporary cement for implant use is shown below. The temporary cement for implant use preferably contains 5 to 500 parts by weight of the acrylic block copolymer (a), 0.05 to 15 parts by weight of the polymerization initiator (c), and 0.05 to 20 parts by weight of the polymerization accelerator (d), with respect to 100 parts by weight of the total amount of the polymerizable monomer (b), and 0 to 250 parts by weight of the filler (e), with respect to 100 parts by weight of the total amount of the acrylic block copolymer (a) and the polymerizable monomer (b). It is more preferable to contain 10 to 250 parts by weight of the acrylic block copolymer (a), 0.1 to 10 parts by weight of the polymerization initiator (c), and 0.1 to 10 parts by weight of the polymerization accelerator (d), with respect to 100 parts by weight of the total amount of the polymerizable monomer (b), and 0 to 100 parts by weight of the filler (e), with respect to 100 parts by weight of the total amount of the acrylic block copolymer (a) and the polymerizable monomer (b).

A suitable configuration example of the mobile tooth-fixing material is shown below. The mobile tooth-fixing material preferably contains 5 to 500 parts by weight of the acrylic block copolymer (a), 0.05 to 15 parts by weight of the polymerization initiator (c), and 0.05 to 20 parts by weight of the polymerization accelerator (d), with respect to 100 parts by weight of the total amount of the polymerizable monomer (b), and 0 to 250 parts by weight of the filler (e), with respect to 100 parts by weight of the total amount of the acrylic block copolymer (a) and the polymerizable monomer (b). It is more preferable to contain 10 to 250 parts by weight of the acrylic block copolymer (a), 0.1 to 10 parts by weight of the polymerization initiator (c), and 0.1 to 10 parts by weight of the polymerization accelerator (d), with respect to 100 parts by weight of the total amount of the polymerizable monomer (b), and 0 to 100 parts by weight of the filler (e), with respect to 100 parts by weight of the total amount of the acrylic block copolymer (a) and the polymerizable monomer (b).

A suitable configuration example of the dental composite resin is shown below. The dental composite resin preferably contains 5 to 250 parts by weight of the acrylic block copolymer (a), 0.05 to 15 parts by weight of the polymerization initiator (c), and 0.05 to 20 parts by weight of the polymerization accelerator (d), with respect to 100 parts by weight of the total amount of the polymerizable monomer (b), and 0 to 500 parts by weight of the filler (e), with respect to 100 parts by weight of the total amount of the acrylic block copolymer (a) and the polymerizable monomer (b). It is more preferable to contain 10 to 250 parts by weight of the acrylic block copolymer (a), 0.1 to 15 parts by weight of the polymerization initiator (c), and 0.1 to 10 parts by weight of the polymerization accelerator (d), with respect to 100 parts by weight of the total amount of the polymerizable monomer (b), and 50 to 250 parts by weight of the filler (e), with respect to 100 parts by weight of the total amount of the acrylic block copolymer (a) and the polymerizable monomer (b).

EXAMPLES

Hereinafter, the present invention is described in detail with reference to examples and comparative examples. However, the present invention is not limited to these examples.

In the following reference examples, the weight-average molecular weights of sampled polymers (polymers that form each block) and the acrylic block copolymer (final polymer) were determined by gel permeation chromatography (hereinafter, referred to as GPC) in terms of polystyrene. The device and conditions employed for GPC measurement were as follows.

<Device and Conditions for GPC Measurement>
Device: GPC system "HLC-8020", manufactured by TOSOH CORPORATION
Separation columns: "TSKgel GMHXL", "G4000HXL", and "G5000HXL", manufactured by TOSOH CORPORATION, connected in series
Eluent: Tetrahydrofuran
Flow rate of eluent: 1.0 ml/minute
Detection method: Differential refractive index (RI)
UV absorbance (Reference Example 4)

Further, in the following reference examples, the component ratio of the respective polymer blocks in the acrylic block copolymer was determined by $^1$H-NMR measurement. The device and condition employed for $^1$H-NMR measurement were as follows.

<Device and Condition for $^1$H-NMR Measurement>
Device: Nuclear magnetic resonance spectrometer "JNM-LA400", manufactured by JEOL Ltd.
Deuterated solvent: Deuterated chloroform The acrylic block copolymer used in this example was produced as follows.

Reference Example 1

Production of the Acrylic Block Copolymer (a)-1

(1) A three-way stopcock was attached to a 1 liter three-necked flask, the inside of which was degassed and substituted by nitrogen. Thereafter, 390 g of toluene, 1.4 ml of N,N',N',N'',N''-pentamethyl diethylene triamine, and 18 ml of a toluene solution containing 11 mmol of isobutylbis(2,6-di-t-butyl-4-methylphenoxy)aluminum was added thereto at room temperature, and 1.7 ml of a mixed solution of cyclohexane and n-hexane containing 2.2 mmol of sec-butyl lithium was further added thereto. 14 ml of methyl methacrylate was added thereto, which was allowed to react at room temperature for 1 hour. 1 g of the reaction solution at that time was collected as Sample 1. Subsequently, the internal temperature of the polymerization solution was cooled to −15° C., and 120 ml of n-butyl acrylate was added dropwise thereto over 6 hours. After completion of addition, 1 g of the reaction solution was collected as Sample 2. Subsequently, 14 ml of methyl methacrylate was added thereto, and the reaction solution was heated to room temperature, followed by stirring for about 10 hours. 1 g of methanol was added to this reaction solution to stop the polymerization. The reaction solution after stopping the polymerization was poured into a large amount of mixed solution of methanol and water (90 mass % of methanol), and the deposited white precipitate was recovered as Sample 3.

(2) Samples 1 to 3 collected or recovered in the above-mentioned step (1) were subjected to GPC measurement and $^1$H-NMR measurement by the above-mentioned method. On the basis of the results, Mw (weight-average molecular weight), Mw/Mn (molecular weight distribution), and the mass ratio between methyl methacrylate polymer (PMMA) block and n-butyl acrylate polymer (PnBA) block were determined for the polymer and the block copolymers obtained at each polymerization step. Thus, it was proved that: the white precipitate finally obtained in the above-mentioned step (1) was a triblock copolymer composed of PMMA-PnBA-PMMA; the overall Mw thereof was 85,000; the Mw/Mn was 1.13; and the ratio of the respective polymer blocks was PMMA(10 mass %)-PnBA(80 mass %)-PMMA(10 mass %), (that is, the total of PMMA was 20 mass %). Further, Sample 1 was PMMA, the Mw thereof was 7,300, and the Mw/Mn thereof was 1.06. Sample 2 was a diblock copolymer of PMMA-PnBA, the Mw thereof was 77,000, and the Mw/Mn thereof was 1.16.

Reference Example 2

Production of the Acrylic Block Copolymer (a)-2

(1) A three-way stopcock was attached to a 1 liter three-necked flask, the inside of which was degassed and substituted by nitrogen. Thereafter, 390 g of toluene, 1.4 ml of N,N',N',N'',N''-pentamethyl diethylene triamine, and 18 ml of a toluene solution containing 11 mmol of isobutylbis(2,6-di-t-butyl-4-methylphenoxy)aluminum was added thereto at room temperature, and 1.7 ml of a mixed solution of cyclohexane and n-hexane containing 2.2 mmol of sec-butyl lithium was further added thereto. 35 ml of methyl methacrylate was added thereto, which was allowed to react at room temperature for 1 hour. 1 g of the reaction solution at that time was collected as Sample 1. Subsequently, the internal temperature of the polymerization solution was cooled to −15° C., and 75 ml of n-butyl acrylate was added dropwise thereto over 5 hours. After completion of addition, 1 g of the reaction solution was collected as Sample 2. Subsequently, 35 ml of methyl methacrylate was added thereto, and the reaction solution was heated to room temperature, followed by stirring for about 10 hours. 1 g of methanol was added to this reaction solution to stop the polymerization. The reaction solution after stopping the polymerization was poured into a large amount of mixed solution of methanol and water (90 mass % of methanol), and the deposited white precipitate was recovered as Sample 3.

(2) Samples 1 to 3 collected or recovered in the above-mentioned step (1) were subjected to GPC measurement and $^1$H-NMR measurement by the above-mentioned method. On the basis of the results, Mw, Mw/Mn, and the mass ratio between methyl methacrylate polymer (PMMA) block and n-butyl acrylate polymer (PnBA) block were determined for the polymer and the block copolymers obtained at each polymerization step. Thus, it was proved that: the white precipitate finally obtained in the above-mentioned step (1) was a triblock copolymer composed of PMMA-PnBA-PMMA; the overall Mw thereof was 85,000; the Mw/Mn was 1.03; and the ratio of the respective polymer blocks was PMMA(25 mass %)-PnBA(50 mass %)-PMMA(25 mass %), (that is, the total of PMMA was 50 mass %). Further, Sample 1 was PMMA, the Mw thereof was 18,000, and the Mw/Mn thereof was 1.05. Sample 2 was a diblock copolymer of PMMA-PnBA, the Mw thereof was 67,000, and the Mw/Mn thereof was 1.14.

Reference Example 3

Production of the Acrylic Block Copolymer (a)-3

(1) A three-way stopcock was attached to a 1 liter three-necked flask, the inside of which was degassed and substituted by nitrogen. Thereafter, 390 g of toluene, 0.95 ml of N,N',N',N",N"-pentamethyl diethylene triamine, and 12 ml of a toluene solution containing 11 mmol of isobutylbis(2,6-di-t-butyl-4-methylphenoxy)aluminum was added thereto at room temperature, and 1.1 ml of a mixed solution of cyclohexane and n-hexane containing 2.2 mmol of sec-butyl lithium was further added thereto. 5 ml of methyl methacrylate was added thereto, which was allowed to react at room temperature for 1 hour. 1 g of the reaction solution at that time was collected as Sample 1. Subsequently, the internal temperature of the polymerization solution was cooled to −15° C., and 97 ml of n-butyl acrylate was added dropwise thereto over 5 hours. After completion of addition, 1 g of methanol was added to this reaction solution to stop the polymerization. The reaction solution after stopping the polymerization was poured into a large amount of mixed solution of methanol and water (90 mass % of methanol), and the deposited liquid white precipitate was recovered as Sample 2.

(2) Samples 1 and 2 collected or recovered in the above-mentioned step (1) were subjected to GPC measurement and $^1$H-NMR measurement by the above-mentioned method. On the basis of the results, Mw, Mw/Mn, and the mass ratio between methyl methacrylate polymer (PMMA) block and n-butyl acrylate polymer (PnBA) block were determined for the polymer and the block copolymer obtained at each polymerization step. Thus, it was proved that: the liquid white precipitate finally obtained in the above-mentioned step (1) was a diblock copolymer composed of PMMA-PnBA; the overall Mw thereof was 125,000; the Mw/Mn was 1.06; and the ratio of the respective polymer blocks was PMMA(5 mass %)-PnBA(95 mass %). Further, Sample 1 was PMMA, the Mw thereof was 6,000, and the Mw/Mn thereof was 1.08.

Reference Example 4

Production of Styrene Block Copolymer 1

(1) 144 g of alpha-methylstyrene, 251 g of cyclohexane, 47.3 g of methyl cyclohexane, and 6.8 g of tetrahydrofuran were added to a pressure-resistant container with a stirring device the inside of which had been substituted by nitrogen. 15.0 ml of sec-butyl lithium (1.3 M cyclohexane solution) was added to this mixed solution, which thereafter was polymerized at −10° C. for 5 hours. After 3 hours from the initiation of the polymerization, the weight-average molecular weight of the poly-alpha-methylstyrene (polymer block A) was 7800 and the polymerization conversion of the alpha-methylstyrene was 90%. Subsequently, 40.5 g of butadiene was added to this reaction solution, which was stirred at −10° C. for 30 minutes, thereby polymerizing butadiene (forming block B1). Thereafter, 1680 g of cyclohexane was added thereto. At this time, the polymerization conversion of the alpha-methylstyrene was 90%, and the 1,4-bond content of the polybutadiene block (B1) determined by the $^1$H-NMR measurement was 19 mol %. Next, 230 g of butadiene was further added to this reaction solution, which was polymerized at 50° C. for 2 hours. The weight-average molecular weight of the polybutadiene block (B2) in the block copolymer (structure: A-B1-B2) obtained by sampling at this time was 33000, and the 1,4-bond content thereof determined by the $^1$H-NMR measurement was 60 mol %.

(2) Subsequently, in accordance with the method disclosed in JP 2007-126527, a solution obtained by dissolving 1.2 g of dichlorodimethylsilane in 30 ml of cyclohexane was added to this polymerization reaction solution, which was stirred at 50° C. for 1 hour. Thus, a poly(alpha-methylstyrene)-polybutadiene-poly(alpha-methylstyrene) triblock copolymer was obtained. The coupling efficiency at this time, as calculated from the UV absorption area ratio of the coupled product (poly(alpha-methylstyrene)-polybutadiene-poly(alpha-methylstyrene) triblock copolymer: A-B1-B2-X-B2-B1-A) and the unreacted block copolymer (poly(alpha-methylstyrene)-polybutadiene block copolymer: A-B1-B2) in GPC, was 97%. Further, as a result of the $^1$H-NMR measurement, the content of alpha-methylstyrene polymer block in the poly(alpha-methylstyrene)-polybutadiene-poly(alpha-methylstyrene) triblock copolymer was 33 wt %, and the 1,4-bond content of the entire butadiene block (that is, block B1+B2) was 53 mol %.

(3) A Ziegler-type hydrogenation catalyst formed from nickel octylate and triethyl aluminum was added to the polymerization reaction solution obtained by the above-mentioned step (2) under an atmosphere of hydrogen, which was allowed to undergo a hydrogenation reaction at 80° C. for 5 hours with a hydrogen pressure of 0.8 MPa. Thereby, a hydrogenated product of the poly(alpha-methylstyrene)-polybutadiene-poly(alpha-methylstyrene) triblock copolymer (which is hereinafter abbreviated as styrene block copolymer 1) was obtained. The resultant styrene block copolymer 1 was subjected to the GPC measurement. As a result, it was proved that: the main component was a hydrogenated product of the poly(alpha-methylstyrene)-polybutadiene-poly(alpha-methylstyrene) triblock copolymer with Mt (the peak top of the average molecular weight)=79000, Mn (the number-average molecular weight)=77000, Mw (the weight-average molecular weight)=78000, and Mw/Mn=1.03, and the content of the coupled product as determined from the UV (254 nm) absorption area ratio in GPC was 97%. Further, the hydrogenation rate of the butadiene block B composed of the block B1 and the block B2 as determined by the $^1$H-NMR measurement was 99%.

Next, the components of the polymerizable compositions of Examples and Comparative Examples are shown below together with abbreviations.

<Polymerizable Monomer (b)>
3G: Triethylene glycol dimethacrylate
D-2.6E: 2,2-bis(4-methacryloyloxypolyethoxyphenyl)propane
TBM: t-Butyl methacrylate
IBM: Isobornyl methacrylate
MDP: 10-methacryloyloxydecyl dihydrogen phosphate
DD: 1,10-decanediol dimethacrylate
<Photopolymerization Initiator (c-1)>
CQ: Camphorquinone
BAPO: Bis-(2,4,6-trimethylbenzoyl)phenylphosphine oxide
<Chemical Polymerization Initiator (c-2)>
BPO: Benzoyl peroxide \<Polymerization Accelerator (d)\>
PDE: N,N-dimethylaminobenzoic acid ethyl ester
DEPT: N,N-di(2-hydroxyethyl)-p-toluidine
TEA: Triethanolamine
TPBSS: Sodium 2,4,6-triisopropylbenzenesulfinate
  \<Filler (e)\>
  Fillers (e)-1 and (e)-2 were obtained by the following production method.
  Filler (e)-1: 3-methacryloyloxypropyltrimethoxysilane-treated silica powder
  Silica powder ("KE-P250", manufactured by NIPPON SHOKUBAI CO., LTD.) was ground with a vibration ball mill. Thus, silica powder was obtained. 100 g of the resultant silica powder, 0.5 g of 3-aminopropyltriethoxysilane, and 200 ml of toluene were put into a 500 ml one-necked eggplant-shaped flask, which was stirred at room temperature for 2 hours. Subsequently, toluene was distilled off under reduced pressure, residue of which was thereafter dried under vacuum at 40° C. for 16 hours, and further dried under vacuum at 90° C. for 3 hours. Thus, 3-methacryloyloxypropyltrimethoxysilane-treated silica powder (filler (e)-1) was obtained. The average particle size of the filler (e)-1 as measured with a laser diffraction particle size distribution analyzer ("SALD-2100", manufactured by SHIMADZU CORPORATION) was 2.4 µm.
  Filler (e)-2: 3-methacryloyloxypropyltrimethoxysilane-treated colloid silica powder
  100 g of colloid silica powder ("Aerosil OX50", manufactured by Japan Aerosil Inc.), 0.5 g of 3-methacryloyloxypropyltrimethoxysilane, and 200 ml of toluene were put into a 500 ml one-necked eggplant-shaped flask, which was stirred at room temperature for 2 hours. Subsequently, toluene was distilled off under reduced pressure, residue of which was thereafter dried under vacuum at 40° C. for 16 hours, and further dried under vacuum at 90° C. for 3 hours. Thus, 3-methacryloyloxypropyltrimethoxysilane-treated colloid silica powder (filler (e)-2) was obtained.
  \<Polymerization Inhibitor\>
BHT: 3, 5-di-t-butyl-4-hydroxytoluene
  The viscosity and forming property of the polymerizable composition obtained in Examples and Comparative Examples, and the flexural modulus, toughness, transparency, color stability, and adhesive properties to tooth structure, metals, and ceramics of a cured product of the composition were measured or evaluated as follows.

Test Example 1

Viscosity

The polymerizable composition was placed on a rheometer (AR2000, manufactured by TA Instruments Japan Inc.) and the viscosity was measured using a 20 mm diameter parallel plate while the temperature was maintained at 25° C. and the plate was rotated in a constant direction at a shearing speed of 1.0 $sec^{-1}$. Those having a viscosity obtained by this measurement of 50 Pa·s or less were considered to have excessively high fluidity, while those having a viscosity of 1000 Pa·s or more were considered to have no fluidity, and thus have poor handling property.

Test Example 2

Forming Property

A 3 mm diameter circle was drawn on dental mixing paper with a size of length: 59 mm×width: 83 mm, and 0.3 g of the polymerizable composition was placed inside the circle. It was erected upright in a constant temperature chamber at 35° C., and was allowed to stand still as it was for 3 minutes. Then, the moving distance of the polymerizable composition from the inside of the circle was measured. This test was performed 3 times, the average of the 3 measured values was taken as a flow score (mm). The greater the flow score, the more likely the polymerizable composition to flow. Those having a flow score obtained from this test of 3 mm or more were considered to have no forming property, and thus have poor handling property.

Test Example 3

Flexural Modulus

The flexural modulus was evaluated by the bending test in accordance with ISO4049. That is, the polymerizable composition produced in each of the following examples was charged into a SUS mold (width: 2 mm×thickness: 2 mm×length: 25 mm), and thereafter it was pressed from above and below each with a slide glass, and both sides thereof were irradiated with light at 5 points on each side for 20 seconds, using a dental visible light unit (JET LITE 3000, manufactured by Morita Corporation). Thus, the polymerizable composition was cured. The resultant cured product was subjected to the bending test using a universal testing machine (autograph AG-100kNI, manufactured by SHIMADZU CORPORATION) at a cross-head speed of 2 mm/min. Thus, the flexural modulus was measured. In order to ensure excellent flexibility, the flexural modulus is preferably not more than 1000 MPa.

Test Example 4

Toughness

In the aforementioned flexural modulus measurement, the test was continued until the cured product reached the yield point or was broken. Specimens that were not broken were evaluated as o, and specimens that were broken were evaluated as x. Specimens that were not broken were determined to have excellent toughness, while specimens that were broken were determined to have low toughness and to be fragile.

Test Example 5

Transparency

The polymerizable composition was charged into a SUS mold (size: 2 mm×diameter: 20 mm), and thereafter it was pressed from above and below each with a slide glass, and both sides thereof were irradiated with light at 6 points on each side for 20 seconds, using a dental visible light unit (JET LITE 3000, manufactured by Morita Corporation). Thus, the polymerizable composition was cured. The transparency (ΔL) of the obtained cured product was measured using a spectrocolorimeter (CM-3610d, light source: D65, manufactured by KONICA MINOLTA HOLDINGS, INC.). In order to ensure high aesthetic value, the transparency (ΔL) is required to be at least 25.

Test Example 6

Color Stability

The specimen produced in Test example 5 was subjected to color measurement using a spectrocolorimeter (CM-3610d, light source: D65, manufactured by KONICA MINOLTA HOLDINGS, INC.), the result of which was taken as the chromaticity before test. Subsequently, the specimen was immersed in distilled water at 70° C. for 10 days, and thereafter was subjected to color measurement again, the result of which was taken as the chromaticity after test. The change of the chromaticity after test from the chromaticity before test was evaluated as a ΔE value. The ΔE value is defined by the following formula. In order to ensure color stability, the ΔE value is required to be 5 or less. The higher the color stability in this test, the more excellent the water resistance.

$$\Delta E=\{(L^*1-L^*2)^2+(a^*1-a^*2)^2+(b^*1-b^*2)^2\}^{1/2},$$

where $L^*1$, $a^*1$, $b^*1$, $L^*2$, $a^*2$, $b^*2$ are values indicating the chromaticity ($L^*$, $a^*$, $b^*$), as measured using a spectrocolorimeter, in color systems of $L^*$, $a^*$, $b^*$. The chromaticity ($L^*1$, $a^*1$, $b^*1$) denote values after immersion in water at 70° C., and the chromaticity ($L^*2$, $a^*2$, $b^*2$) denote values before immersion in water at 70° C.

Test Example 7

Tensile Bond Strength to Tooth Structure (Bovine Enamel/Dentin)

The labial surface of a bovine mandibular incisor was ground with #80 silicon carbide paper (manufactured by NIHON KENSHI CO., LTD.) under running water to form a flat surface of enamel or a flat surface of dentin. Each flat surface was further ground with #1000 silicon carbide paper (manufactured by NIHON KENSHI CO., LTD.) under running water, and thereafter water on the surface was blown off using a dental air syringe.

An adhesive tape with a thickness of about 150 µm having a 3 mm diameter circular hole was attached to each flat surface, thereby defining an adhesive area. The following dental adhesive agent 1 was applied to the inside of the circular hole using a brush, which was left standing for 30 seconds. Thereafter, it was dried with an air syringe until the fluidity of the applied dental adhesive agent 1 was lost. Subsequently, the polymerizable composition was charged into the circular hole on the surface coated with the dental adhesive agent 1, and excess of the polymerizable composition overflowing the circular hole was removed with a razor blade so that a smooth surface was obtained. Thereafter, the polymerizable composition was cured by irradiation with light for 30 seconds using a dental visible light unit (JET LITE 3000, manufactured by Morita Corporation). One end (circular cross section) of a stainless steel cylindrical rod (diameter: 7 mm, length: 2.5 cm) was bonded to the resultant cured product in which an unpolymerized layer of the polymerizable composition was still left, using a commercially available dental resin cement (Panavia 21, manufactured by KURARAY MEDICAL INC.). After bonding, this sample was allowed to stand still for 30 minutes at room temperature, which was then immersed in distilled water. 5 bond test samples were produced in total, and all the samples immersed in distilled water were kept in a constant temperature chamber maintained at 37° C. for 24 hours.

The tensile bond strength of the above-mentioned bond test samples was measured using a universal testing machine (autograph AG-100kNI, manufactured by SHIMADZU CORPORATION) at a cross-head speed of 2 mm/min, and the average of the results was taken as the tensile bond strength.

Dental Adhesive Agent 1:
A mixture composed of:

bis-GMA (2,2-bis[4-(3-methacryloyloxy-2-hydroxypropoxy)phenyl]propane) 5 parts by weight
801 (1,2-bis(3-methacryloyloxy-2-hydroxypropoxy) ethane) 25 parts by weight
HEMA (2-hydroxyethyl methacrylate) 25 parts by weight
MDP 10 parts by weight
CQ 1.5 parts by weight
BAPO 1.0 part by weight
PDE 1.0 part by weight
DEPT 1.5 parts by weight
BHT 0.05 part by weight
Distilled water 15.0 parts by weight
Ethanol 15.0 parts by weight Test Example 8

Adhesive Properties to Metals

A titanium strip (Titanium 100, manufactured by SHOFU INC., titanium content: at least 99.5%) with dimensions: 10 mm×thickness: 5 mm was ground with #1000 silicon carbide paper (manufactured by NIHON KENSHI CO., LTD.) under running water to form a smooth surface, and thereafter water on the surface was blown off with a dental air syringe.

The following dental adhesive agent 2 was applied to the smooth surface of the titanium strip, followed by air drying. Thereafter, an adhesive tape with a thickness of about 150 µm having a 5 mm diameter circular hole was attached thereto, thereby defining an adhesive area. Subsequently, the polymerizable composition was charged into the circular hole on the surface coated with the dental adhesive agent 2, and excess of the polymerizable composition overflowing the circular hole was removed with a razor blade so that a smooth surface was obtained. Thereafter, the polymerizable composition was cured by irradiation with light for 30 seconds using a dental visible light unit (JET LITE 3000, manufactured by Morita Corporation). One end (circular cross section) of a stainless steel cylindrical rod (diameter: 7 mm, length: 2.5 cm) was bonded to the resultant cured product in which an unpolymerized layer of the polymerizable composition was still left, using a commercially available dental resin cement (Panavia 21, manufactured by KURARAY MEDICAL INC.). After bonding, this sample was allowed to stand still for 30 minutes at room temperature, which was then immersed in distilled water. 5 bond test samples were produced in total, and all the samples immersed in distilled water were kept in a constant temperature chamber maintained at 37° C. for 24 hours.

The tensile bond strength of the above-mentioned bond test samples was measured using a universal testing machine (autograph AG-100kNI, manufactured by SHIMADZU CORPORATION) at a cross-head speed of 2 mm/min, and the average of the results was taken as the tensile bond strength.

Dental Adhesive Agent 2:
A mixture composed of
Acetone 99.0%
6-(4-vinylbenzyl-n-propyl)amino-1,3,5-triazine-2,4-dithion 0.6%
10-methacryloyloxydecyl dihydrogen phosphate 0.4%

Test Example 9

Adhesive Properties to Ceramics

The above-mentioned test was conducted in the same manner as in Test example 8 except that Titanium 100 used in Test example 8 was changed to a ceramic strip (VITA CELAY, manufactured by VITA), and the dental adhesive agent 2 was changed to the following dental adhesive agent 3.

Dental Adhesive Agent 3:
A mixture composed of
Ethanol 95.0%
3-methacryloyloxypropyltrimethoxysilane 5.0%
10-methacryloyloxydecyl dihydrogen phosphate 1.0%

Examples 1 to 16 and Comparative Examples 1 to 6

Preparation of Polymerizable Composition

The raw materials shown in Table 1 to Table 4 were mixed at room temperature to prepare a paste A (and a paste B), and then the properties thereof were investigated in accordance with the method described above in Test examples 1 to 9. Table 1 to Table 4 show the results.

TABLE 1

| | | EX. 1 | EX. 2 | EX. 3 | EX. 4 | EX. 5 | EX. 6 | EX. 7 | EX. 8 | EX. 9 | EX. 10 | EX. 11 |
|---|---|---|---|---|---|---|---|---|---|---|---|---|
| Raw materials | Acrylic block copolymer (a)-1 | 45 | 40 | 45 | 45 | | | | | | 30 | 25 |
| | Acrylic block copolymer (a)-2 | | | | | 30 | 30 | | | 10 | | |
| | Acrylic block copolymer (a)-3 | | | | | | | 70 | 60 | 30 | | |
| | Styrene block copolymer 1 | | | | | | | | | | 5 | |
| | Styrene block copolymer 2 [1)] | | | | | | | | | | | 5 |
| | 3G (b)-1 | 15 | 10 | 15 | 15 | 15 | 10 | 15 | 15 | 15 | 10 | 10 |
| | D2.6E (b)-2 | | | | | | 5 | 5 | 5 | | | |
| | TBM (b)-3 | 40 | 25 | 30 | 30 | 55 | 50 | | | 35 | 20 | 20 |
| | IBM (b)-4 | | 25 | | | | | 10 | 15 | | 10 | 10 |
| | MDP (b)-5 | | | 10 | 10 | | 5 | | 5 | 10 | 10 | 10 |
| | DD (b-)6 | | | | | | | | | | 5 | 5 |
| | CQ (c-1)-1 | | 1.0 | 0.5 | 0.5 | | 1.5 | | 1.5 | 1.0 | 0.5 | 0.5 |
| | BAPO (c-1)-2 | 2.5 | 1.0 | 2.0 | 2.0 | 3.0 | 1.5 | 3.0 | 2.0 | 1.5 | 2.0 | 2.0 |
| | PDE (d)-1 | | 1.0 | 0.5 | 0.5 | | 1.5 | | 1.5 | 1.0 | 0.5 | 0.5 |
| | Filler (e)-1 | | | | 25 | | 10 | | 50 | | | |
| | Filler (e)-2 | | | 10 | 5.0 | | 3.0 | | 5.0 | 5.0 | 10 | 10 |
| | BHT | 0.05 | 0.05 | 0.05 | 0.05 | 0.05 | 0.05 | 0.05 | 0.05 | 0.05 | 0.05 | 0.05 |
| Properties | Viscosity (Pa·s) | 750 | 680 | 790 | 870 | 780 | 790 | 810 | 910 | 780 | 870 | 920 |
| | Forming property: Flow score (mm) | 0 | 0 | 0 | 0 | 1 | 0 | 1 | 0 | 0 | 0 | 0 |
| | Flexural modulus (MPa) | 120 | 180 | 240 | 390 | 330 | 440 | 90 | 380 | 310 | 580 | 670 |
| | Toughness | ○ | ○ | ○ | ○ | ○ | ○ | ○ | ○ | ○ | ○ | ○ |
| | Transparency ΔL | 50 | 48 | 42 | 35 | 53 | 39 | 41 | 34 | 47 | 38 | 34 |
| | Color stability ΔE | 1.6 | 1.7 | 1.4 | 1.9 | 1.4 | 1.7 | 2.4 | 2.1 | 1.4 | 1.8 | 1.5 |
| | Tensile bond strength to bovine enamel (MPa) | 9.5 | 8.2 | 10.3 | 11.3 | 9.2 | 9.5 | 7.8 | 8.1 | 9.3 | 8.9 | 8.3 |
| | Tensile bond strength to bovine dentin (MPa) | 7.1 | 7.2 | 8.5 | 8.3 | 7.7 | 8.4 | 7.1 | 7.6 | 8.2 | 8.1 | 7.9 |
| | Tensile bond strength to titanium alloy (MPa) | 7.3 | 7.2 | 8.6 | 8.9 | 7.4 | 8.2 | 7.2 | 7.7 | 8.3 | 7.8 | 7.6 |
| | Tensile bond strength to ceramics (MPa) | 8.7 | 8.9 | 9.8 | 9.9 | 9.5 | 9.7 | 8.1 | 8.3 | 8.9 | 8.3 | 8.1 |

[1)] Styrene block copolymer 2: Hydrogenated product of polystyrene-polybutadiene-polystyrene (SEPTON8007, manufactured by KURARAY CO., LTD.)

TABLE 2

| | | C. EX. 1 | C. EX. 2 | C. EX. 3 |
|---|---|---|---|---|
| Raw materials | Acrylic polymer 1 [2)] | | 20 | |
| | Acrylic copolymer 1 [3)] | | | 10 |
| | 3G (b)-1 | 15 | 15 | 15 |
| | TBM (b)-3 | 85 | 65 | 75 |
| | CQ (c-1) | 1.0 | 1.0 | 1.0 |
| | BAPO (c-1) | 1.0 | 1.0 | 1.0 |
| | PDE (d)-1 | 1.0 | 1.0 | 1.0 |
| | Filler (e)-1 | 20 | | |
| | Filler (e)-2 | 5 | | |
| | BHT | 0.05 | 0.05 | 0.05 |
| Properties | Viscosity (Pa·s) | 260 | 4,800 | 7,300 |
| | Forming property: Flow score (mm) | 18 | 0 | 0 |
| | Flexural modulus (MPa) | 2,800 | 1,800 | 2,200 |
| | Toughness | x | x | x |
| | Transparency ΔL | 37 | 18 | 13 |
| | Color stability ΔE | 2.3 | 2.5 | 2.9 |
| | Tensile bond strength to bovine enamel (MPa) | 2.4 | 2.8 | 2.9 |
| | Tensile bond strength to bovine dentin (MPa) | 1.8 | 2.1 | 2.5 |
| | Tensile bond strength to titanium alloy (MPa) | 2.1 | 2.3 | 2.2 |
| | Tensile bond strength to ceramics (MPa) | 2.5 | 2.3 | 2.6 |

[2)] Acrylic polymer 1: Polybutylmethacrylate (Hi Pearl M-6003, manufactured by Negami chemical industrial co., ltd, molecular weight: 250,000 to 350,000)

[3)] Acrylic copolymer 1: Poly(methyl methacrylate/ethyl methacrylate) (Hi Pearl M-4501, manufactured by Negami chemical industrial co., ltd, molecular weight: 650,000 to 1,000,000)

TABLE 3

|  |  | EX. 12 | | EX. 13 | | EX. 14 | | EX. 15 | | EX. 16 | | EX. 17 | | EX. 18 | |
|---|---|---|---|---|---|---|---|---|---|---|---|---|---|---|---|
|  |  | A | B | A | B | A | B | A | B | A | B | A | B | A | B |
| Raw materials | Acrylic block copolymer (a)-1 | 45 | 45 | 40 | 40 |  |  |  |  |  |  |  |  |  |  |
|  | Acrylic block copolymer (a)-2 |  |  |  |  | 30 | 30 | 30 | 30 |  |  |  |  | 20 |  |
|  | Acrylic block copolymer (a)-3 |  |  |  |  |  |  |  |  | 70 | 70 | 60 | 60 |  | 70 |
|  | 3G (b)-1 | 15 | 15 | 15 | 15 | 15 | 15 | 15 | 10 | 15 | 15 | 20 | 20 | 15 | 5 |
|  | D2.6E (b)-2 |  |  |  |  |  |  |  | 5 | 10 | 10 |  | 10 |  | 15 |
|  | TBM (b)-3 | 40 | 40 | 25 | 25 | 55 | 55 | 45 | 55 |  |  |  |  | 55 |  |
|  | IBM (b)-4 |  |  | 10 | 20 |  |  |  |  | 5 | 5 | 5 | 10 |  | 10 |
|  | MDP (b)-5 |  |  | 10 |  |  |  | 10 |  |  |  | 15 |  | 10 |  |
|  | CQ (c-1)-1 |  |  | 0.25 |  | 0.25 |  | 0.5 |  | 0.25 |  | 0.5 |  |  |  |
|  | BAPO (c-1)-2 | 2.5 |  | 1.5 |  | 1.5 |  | 1.5 |  | 1.0 |  | 1.5 |  | 2.0 |  |
|  | BPO (c-2) | 1.5 |  |  | 2.0 |  | 1.5 |  | 2.0 |  | 1.5 |  | 3.0 |  | 2.5 |
|  | PDE (d)-1 |  |  |  | 0.5 |  | 0.5 |  | 0.5 |  | 0.25 |  | 0.5 |  |  |
|  | DEPT (d)-2 |  | 1.0 |  | 1.5 |  | 1.0 |  | 1.5 |  | 1.0 |  | 1.0 |  | 1.5 |
|  | TEA (d)-3 |  |  |  | 0.1 |  | 0.25 |  | 0.25 |  | 0.1 |  | 0.1 |  |  |
|  | TPBSS (d)-4 |  |  |  | 0.1 |  | 0.25 |  | 0.25 |  | 0.1 |  | 0.1 |  |  |
|  | Filler (e)-1 |  |  | 25 | 15 |  |  | 20 | 10 |  |  | 25 | 20 |  |  |
|  | Filler (e)-2 |  |  | 5 | 5 |  |  | 3 | 3 |  |  | 5 | 5 | 5 | 5 |
|  | BHT | 0.05 | 0.05 | 0.05 | 0.05 | 0.05 | 0.05 | 0.05 | 0.05 | 0.05 | 0.05 | 0.05 | 0.05 | 0.05 | 0.05 |
| Properties | Viscosity (Pa·s) | 760 | | 860 | | 870 | | 930 | | 790 | | 920 | | 810 | |
|  | Forming property: Flow score (mm) | 0 | | 0 | | 0 | | 0 | | 0 | | 0 | | 0 | |
|  | Flexural modulus (MPa) | 150 | | 320 | | 290 | | 420 | | 110 | | 190 | | 260 | |
|  | Toughness | ○ | | ○ | | ○ | | ○ | | ○ | | ○ | | ○ | |
|  | Transparency ΔL | 50 | | 36 | | 51 | | 41 | | 42 | | 30 | | 38 | |
|  | Color stability ΔE | 2.5 | | 2.7 | | 2.3 | | 2.4 | | 2.9 | | 2.7 | | 2.8 | |
|  | Tensile bond strength to bovine enamel (MPa) | 9.8 | | 11.5 | | 9.3 | | 10.3 | | 8.1 | | 9.1 | | 9.2 | |
|  | Tensile bond strength to bovine dentin (MPa) | 8.1 | | 8.4 | | 8.1 | | 8.9 | | 8.0 | | 8.8 | | 8.7 | |
|  | Tensile bond strength to titanium alloy (MPa) | 8.6 | | 8.8 | | 7.7 | | 9.1 | | 8.2 | | 8.9 | | 8.6 | |
|  | Tensile bond strength to ceramics (MPa) | 9.3 | | 9.8 | | 8.6 | | 10.3 | | 9.4 | | 9.8 | | 9.7 | |

TABLE 4

|  |  | EX. 19 | | EX. 20 | | C. EX. 4 | | C. EX. 5 | | C. EX. 6 | |
|---|---|---|---|---|---|---|---|---|---|---|---|
|  |  | A | B | A | B | A | B | A | B | A | B |
| Raw materials | Acrylic block copolymer (a)-1 | 45 | 25 | 45 | 25 |  |  |  |  |  |  |
|  | Acrylic polymer 1 [2)] |  |  |  |  |  |  | 20 | 20 |  |  |
|  | Acrylic copolymer 1 [3)] |  |  |  |  |  |  |  |  | 10 | 10 |
|  | Styrene block copolymer 1 |  | 5 |  |  |  |  |  |  |  |  |
|  | Styrene block copolymer 2 [1)] |  |  |  | 5 |  |  |  |  |  |  |
|  | 3G (b)-1 | 15 | 15 | 15 | 10 | 15 | 15 | 15 | 15 | 15 | 15 |
|  | TBM (b)-3 | 40 | 25 | 40 | 25 | 85 | 85 | 65 | 65 | 75 | 75 |
|  | IBM (b)-4 |  |  | 20 | 25 |  |  |  |  |  |  |
|  | DD (b-)6 |  |  | 10 | 5 |  |  |  |  |  |  |
|  | CQ (c-1)-1 |  |  |  |  | 0.25 |  | 0.25 |  | 0.25 |  |
|  | BAPO (c-1)-2 | 2.5 |  | 2.5 |  | 1.5 |  | 1.5 |  | 1.5 |  |
|  | BPO (c-2) | 1.5 |  | 1.5 |  |  | 1.5 |  | 1.5 |  | 1.5 |
|  | PDE (d)-1 |  |  |  |  |  | 0.5 |  | 0.5 |  | 0.5 |

TABLE 4-continued

|  |  | EX. 19 | | EX. 20 | | C. EX. 4 | | C. EX. 5 | | C. EX. 6 | |
|---|---|---|---|---|---|---|---|---|---|---|---|
|  |  | A | B | A | B | A | B | A | B | A | B |
|  | DEPT (d)-2 |  | 1.0 |  | 1.0 |  | 1.0 |  | 1.0 |  | 1.0 |
|  | TEA (d)-3 |  |  |  |  |  | 0.25 |  | 0.25 |  | 0.25 |
|  | TPBSS (d)-4 |  |  |  |  |  | 0.25 |  | 0.25 |  | 0.25 |
|  | Filler (e)-1 |  |  |  |  | 20 | 20 | 20 | 20 | 20 | 20 |
|  | Filler (e)-2 |  |  | 5 | 5 | 5 | 5 | 5 | 5 | 5 | 5 |
|  | BHT | 0.05 | 0.05 | 0.05 | 0.05 | 0.05 | 0.05 | 0.05 | 0.05 | 0.05 | 0.05 |
| Properties | Viscosity (Pa·s) | 800 |  | 920 |  | 280 |  | 5,200 |  | 7,600 |  |
|  | Forming property: Flow score (mm) | 0 |  | 0 |  | 14 |  | 0 |  | 0 |  |
|  | Flexural modulus (MPa) | 230 |  | 290 |  | 2,900 |  | 1,310 |  | 2,400 |  |
|  | Toughness | ○ |  | ○ |  | x |  | x |  | x |  |
|  | Transparency ΔL | 47 |  | 45 |  | 28 |  | 19 |  | 16 |  |
|  | Color stability ΔE | 2.8 |  | 2.7 |  | 2.1 |  | 2.8 |  | 3.1 |  |
|  | Tensile bond strength to bovine enamel (MPa) | 9.0 |  | 9.3 |  | 2.6 |  | 3.1 |  | 2.8 |  |
|  | Tensile bond strength to bovine dentin (MPa) | 8.3 |  | 8.4 |  | 2.0 |  | 2.2 |  | 2.3 |  |
|  | Tensile bond strength to titanium alloy (MPa) | 8.2 |  | 8.1 |  | 2.0 |  | 2.1 |  | 2.4 |  |
|  | Tensile bond strength to ceramics (MPa) | 9.1 |  | 9.5 |  | 2.4 |  | 2.5 |  | 2.9 |  |

[1] Refer to the note below Table 1
[2, 3] Refer to the notes below Table 2

It can be seen from the results shown in Table 1 to Table 4 that the polymerizable composition containing an acrylic block copolymer of each Example has appropriate viscosity and forming property and excellent handling property before curing compared to the polymerizable compositions containing no acrylic block copolymer of the Comparative Examples. Further, the polymerizable composition containing an acrylic block copolymer of each Example has low flexural modulus, and shows no breakage, thus having excellent flexibility. Furthermore, the polymerizable composition containing an acrylic block copolymer of each Example has high transparency and shows less color change, resulting in excellent aesthetic value. Moreover, the polymerizable composition containing an acrylic block copolymer of each Example has adhesive properties to tooth structure and adhesive properties to titanium and ceramics. From above, it can be seen that the polymerizable composition containing an acrylic block copolymer according to the present invention can be suitably applied to biological tissues and is optimally used as a temporary cement for implant use and a mobile tooth-fixing material.

INDUSTRIAL APPLICABILITY

The polymerizable composition of the present invention can be suitably applied to biological tissues (such as teeth and bones, particularly teeth). Specifically, it is optimally used as a temporary cement for implant use and a mobile tooth-fixing material. It also can be suitably used as a dental cement and a dental composite resin.

The invention claimed is:

1. A polymerizable composition comprising:
   an acrylic block copolymer (a) comprising at least one polymer block A that mainly comprises a (meth)acrylic acid ester unit and that functions as a hard segment and at least one polymer block B that mainly comprises an acrylic acid ester unit and that functions as a soft segment;
   a polymerizable monomer (b) comprising a phosphoric acid group, and
   a polymerization initiator (c),
   wherein:
   the acrylic block copolymer (a) has a molecular weight distribution Mw/Mn of 1.0 to 1.5;
   the (meth)acrylic acid ester is at least one selected from the group consisting of methyl methacrylate, ethyl methacrylate, n-propyl methacrylate, isopropyl methacrylate, n-butyl methacrylate, s-butyl methacrylate, t-butyl methacrylate, isobutyl methacrylate, n-hexyl methacrylate, cyclohexyl methacrylate, isobornyl methacrylate, benzyl methacrylate, and phenyl methacrylate,
   the acrylic acid ester is at least one selected from the group consisting of methyl acrylate, ethyl acrylate, n-propyl acrylate, isopropyl acrylate, n-butyl acrylate, isobutyl acrylate, s-butyl acrylate, t-butyl acrylate, n-hexyl acrylate, cyclohexyl acrylate, 2-ethylhexyl acrylate, dodecyl acrylate, lauryl acrylate, stearyl acrylate and 2-methoxyethyl acrylate; and
   the acrylic block copolymer (a) is inactive against a polymerizable group of the polymerizable monomer (b).

2. The polymerizable composition according to claim 1, wherein the acrylic block copolymer (a) has a molecular weight distribution Mw/Mn of 1.0 to 1.3.

3. The polymerizable composition according to claim 1, wherein the polymerizable monomer (b) is a (meth)acrylate polymerizable monomer.

4. The polymerizable composition according to claim 1, further comprising:
   a polymerization accelerator (d).

5. The polymerizable composition according to claim 1, further comprising:
   a filler (e).

6. The polymerizable composition according to claim 1, wherein said composition is suitable for application to biological tissues.

7. A dental cement comprising the polymerizable composition according to claim 1.

8. The dental cement according to claim 7, wherein the dental cement is a temporary cement for implant use.

9. A dental mobile tooth-fixing material comprising the polymerizable composition according to claim 1.

10. A dental composite resin comprising the polymerizable composition according to claim 1.

11. The polymerizable composition according to claim 1, wherein the polymerizable monomer (b) comprising a phosphoric acid group is at least one selected from the group consisting of 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyicosyl dihydrogen phosphate, bis[2-(meth)acryloyloxyethyl]hydrogen phosphate, bis[4-(meth)acryloyloxybutyl]hydrogen phosphate, bis[6-(meth)acryloyloxyhexyl]hydrogen phosphate, bis[8-(meth)acryloyloxyoctyl]hydrogen phosphate, bis[9-(meth)acryloyloxynonyl]hydrogen phosphate, bis[10-(meth)acryloyloxydecyl]hydrogen phosphate, 1,3-di(meth)acryloyloxypropyl dihydrogen phosphate, 2-(meth)acryloyloxyethylphenyl hydrogen phosphate, 2-(meth)acryloyloxyethyl-2-bromoethyl hydrogen phosphate, bis[2-(meth)acryloyloxy-(1-hydroxymethyl)ethyl]hydrogen phosphate, and their acid chlorides, alkali metal salts, and ammonium salts.

12. The polymerizable composition according to claim 1, wherein the polymerizable monomer (b) comprising a phosphoric acid group comprises in its molecule an alkylene group having 8 to 12 carbon atoms in the main chain.

13. The polymerizable composition according to claim 1, wherein the (meth)acrylic acid ester is at least one selected from the group consisting of methyl methacrylate, isobornyl methacrylate, and t-butyl methacrylate and the acrylic acid ester unit is at least one selected from the group consisting of n-butyl acrylate and 2-ethylhexyl acrylate.

14. The polymerizable composition according to claim 1, wherein acrylic block copolymer (a) consists of polymer block A and polymer block B, and wherein the content of polymer block A in acrylic block copolymer (a) is 1 to 75 wt % and the content of polymer block B in acrylic block copolymer (a) is 25 to 99 wt %.

15. The polymerizable composition according to claim 11, wherein
the (meth)acrylic acid ester is at least one selected from the group consisting of methyl methacrylate, isobornyl methacrylate, and t-butyl methacrylate and the acrylic acid ester unit is at least one selected from the group consisting of n-butyl acrylate and 2-ethylhexyl acrylate, and
acrylic block copolymer (a) consists of polymer block A and polymer block B, and wherein the content of polymer block A in acrylic block copolymer (a) is 1 to 75 wt % and the content of polymer block B in acrylic block copolymer (a) is 25 to 99 wt %.

16. The polymerizable composition according to claim 1, wherein acrylic block copolymer (a) consists of polymer block A and polymer block B, and wherein polymer block A comprises at least 90 wt % of said (meth)acrylic acid ester unit based on the weight of all monomer units therein and polymer block B comprises at least 90 wt % of said acrylic acid ester unit based on the weight of all monomer units therein.

17. The polymerizable composition according to claim 15, wherein acrylic block copolymer (a) consists of polymer block A and polymer block B, and wherein polymer block A comprises at least 90 wt % of said (meth)acrylic acid ester unit based on the weight of all monomer units therein and polymer block B comprises at least 90 wt % of said acrylic acid ester unit based on the weight of all monomer units therein.

18. The polymerizable composition according to claim 1, wherein acrylic block copolymer (a) consists of polymer block A and polymer block B, and wherein polymer block A consists of said (meth)acrylic acid ester unit and polymer block B consists of said acrylic acid ester unit.

* * * * *